(12) United States Patent
Pisharodi

(10) Patent No.: US 6,402,755 B1
(45) Date of Patent: Jun. 11, 2002

(54) PLATE SYSTEM FOR BRIDGING AND STABILIZING SPACED APART BONE SEGMENTS

(75) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 0 days.

(21) Appl. No.: 09/746,750

(22) Filed: Dec. 21, 2000

(51) Int. Cl.[7] ............................................... A61B 17/70
(52) U.S. Cl. ............................. 606/71; 606/61; 606/73; 623/17.16; 623/17.11
(58) Field of Search .............................. 606/60, 61, 59, 606/70, 71, 72, 73, 53; 623/17.11, 17.15, 17.16

(56) References Cited

U.S. PATENT DOCUMENTS

| | | | |
|---|---|---|---|
| 4,892,545 A | * 1/1990 | Day et al. | 606/61 |
| 5,458,641 A | * 10/1995 | Ramirez Jimenez | 623/17.16 |
| 5,810,816 A | * 9/1998 | Roussouly et al. | 606/61 |
| 6,030,389 A | * 2/2000 | Wagner et al. | 606/71 |
| 6,193,721 B1 | * 2/2001 | Michelson | 606/70 |

* cited by examiner

*Primary Examiner*—Pedro Philogene
(74) *Attorney, Agent, or Firm*—Jackson Walker L.L.P.

(57) ABSTRACT

A medical appliance adapted to bridge and stabilize spaced apart bone segments having outside, ledge and inside surfaces. The appliance has an elongate bottom plate, an elongate top plate, and a locking member. The bottom plate is attachable to the ledge surface of the bone and has a bottom base plate, a plurality of screw barrels extending from the bottom base plate in a first direction for receiving barrel screws, and a plurality of openings in the base plate for rotatably retaining the screw barrels. The elongate top plate has a top plate base, a plurality of slots aligned to allow the barrel screws to engage the screw barrels of the bottom plate. The locking member is dispoaed in a countersink to engage the bone screws such that axial and rotational movement of the bone screws may be restricted. The screw barrels are equipped with an angle first end and a riveted second end to restrain screw movement but allow the screws to engage the barrels at various angles. A locking member includes a locking ring having a plurality of tapered rachet teeth on an interior surface.

24 Claims, 5 Drawing Sheets

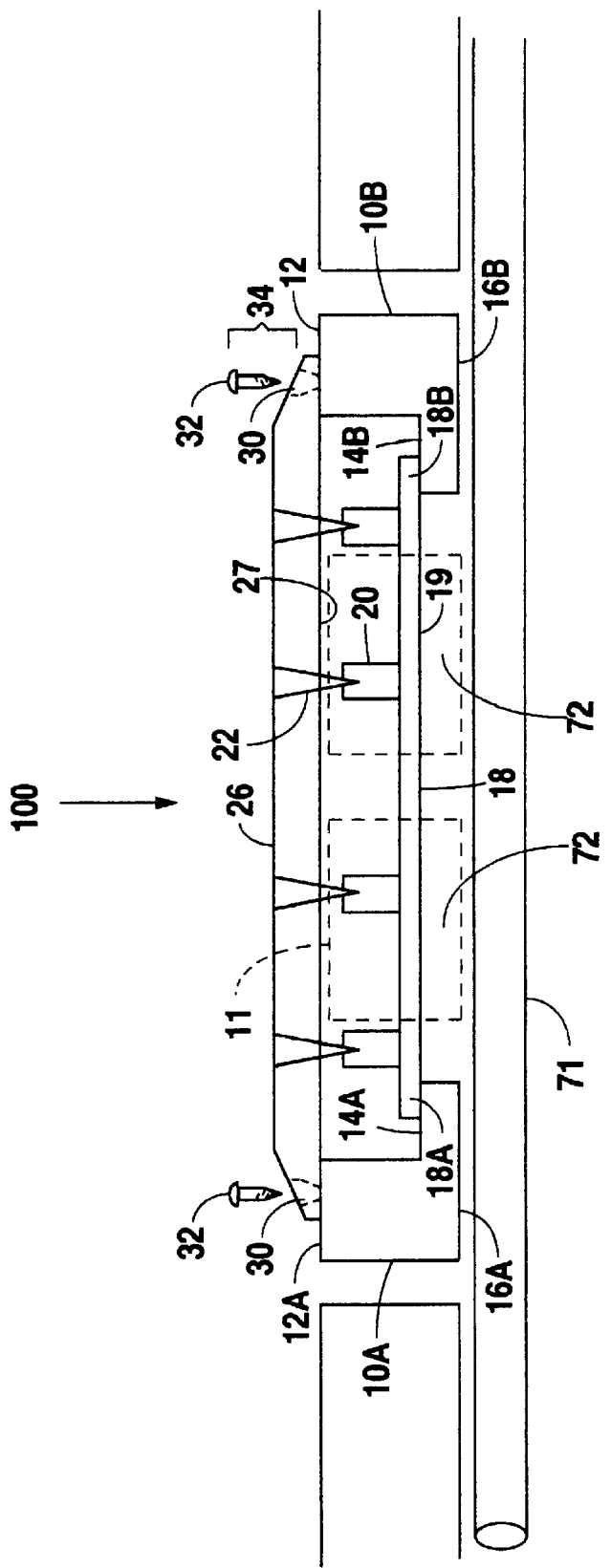

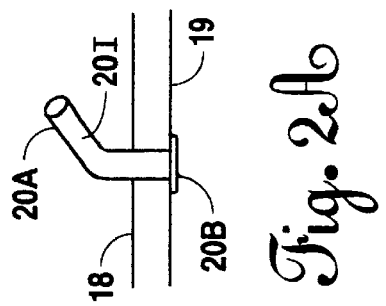
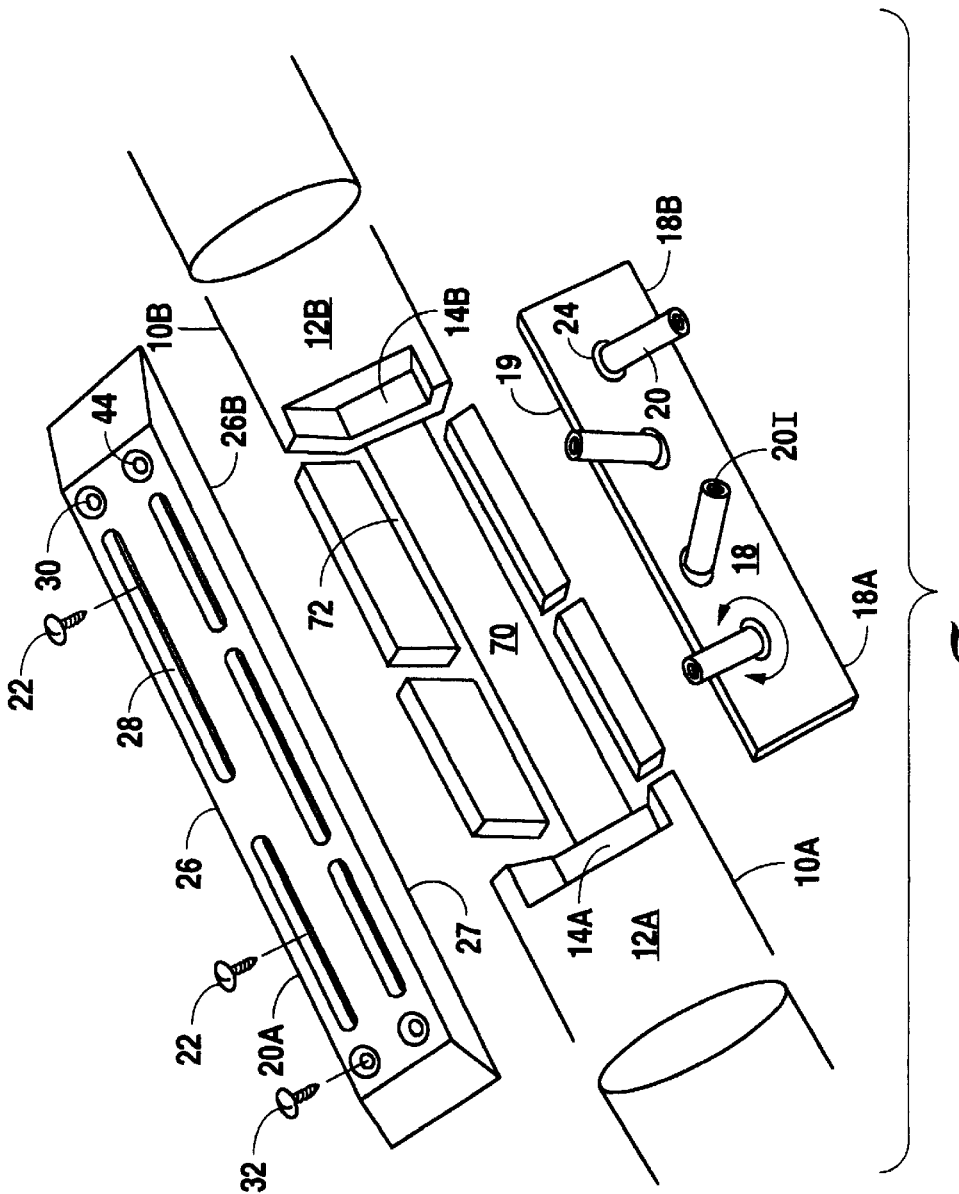

PLATE SYSTEM FOR BRIDGING AND STABILIZING SPACED APART BONE SEGMENTS

BACKGROUND OF THE INVENTION

The present invention relates to a medical appliance and more particularly to a medical appliance and method for bridging and stabilizing spaced apart bone segments.

While the present invention is intended for use with vertebrae, it should be understood that any spaced apart bone segment may utilize the present invention. The spine is a flexible structure comprised of thirty-three vertebrae. The vertebrae are separated and cushioned from each other by fibrous cartilage in structures called intervertebral disks. If the spine is injured or becomes diseased, surgical intervention involving removal of one or more of these disks and fusion of the adjacent vertebrae, may be indicated. Such disk injuries can happen in the neck, in the thoracic region and in the lumbar region. The more frequent injuries are in the lower lumbar and in the lower cervical regions.

Treatment of a herniated disk in the neck and in the lumbar region continues to be a challenging field of medicine. The classical treatment for a ruptured disk continues to be removal of the disk from between the vertebrae. By this process of removing the disk, overall spinal instability is increased. This may aggravate the patient to some degree after the operation. Another procedure previously employed is to replace the disk space with a bone graft, bringing about fusion of the vertebrae above and below the disk, eliminating the empty space between the vertebrae and improving stability.

Theoretically a diskectomy with fusion is a satisfactory procedure, though not ideal because the replaced bone does not have the principal functions of the cartilage tissue of the disk. This fusion procedure is technically demanding and has medical complications because of several physiological factors.

It must be remembered that the disk primarily serves as a mechanical cushion while permitting limited mobility. For any replacement system for a disk to be truly effective, it must allow for mobility within the natural limits of the original disk. In other words, the replacement should match appropriate joint rheology (movement behavior). The natural disk allows about 11 degrees of flexion-extension, limited lateral bending of 3 to 5 degrees, and very restricted rotation of about 1 degree.

Various prosthetic devices and implants are disclosed in the art, but all are characterized by compromises to the full functions of a natural disk discussed above. Examples of the prior art include the following U.S. Pat. Nos.: 5,893,890; 5,693,100; 5,658,336; 5,653,761; 5,653,762; 5,390,683; 5,171,278; and 5,123,926. The specification and drawings of U.S. patent application Ser. No. 09/627,261 is herein incorporated b y reference. The present invention provides stabilization of spaced apart bone segments while still allowing some flexion and rearward extension of the bones with some lateral displacement. The present invention is particularly useful to stabilize adjacent vertebrae in the human spine.

SUMMARY OF THE INVENTION

Accordingly, the present invention provides a medical appliance and method for bridging and stabilizing spaced apart bone segments. The present invention uses a rigid, elongate bottom plate to span space between bone segments and to attach to a ledge surface of each bone such that a plurality of screw barrels rotatably engaging a plurality of openings in the bottom plate base may receive a plurality of barrel screws to couple the bottom plate to a rigid, elongate top plate. The top plate is attachable to an outside surface of each bone segment and has a top plate base having a plurality of slots for rotatably receiving screw barrels. The slots are aligned to allow barrel screws to engage the screw barrels such that the top and bottom plate may be coupled together.

The top plate is also equipped with a plurality of countersinks. The countersinks receive bone screws such that the top plate may be attached to the outside surface of each bone segment. The present invention also has a locking member disposed in the countersink or attached to the bone screw for securing the bone screws to the medical appliance such that axial and rotational movement of the bone screws is restricted.

The screw barrels of the present invention may be equipped with an angled first end and a riveted second end such that movement of the screw barrels may be restricted in a first and second direction while still allowing the screw barrels to rotate within the openings to allow the barrel screws to engage the screw barrels at various angles. A locking ring having a plurality of tapered rachet teeth on an interior surface may be used to secure the bone screws to the medical appliance. The teeth engage a serrated neck of each bone screw upon insertion of each bone screw into a countersink, thus securing the bone screws.

The configuration of each locking ring and each countersink may vary depending on the application of the medical appliance. They may have a substantially circular configuration or a non-circular configuration that allow them to work in concert to provide varying degrees of axial and rotational movement for the bone screws. In one embodiment of the present invention, the locking ring may be attached to the bone screw to provide a preassembled locking member.

Another embodiment of the present invention provides a pre-assembled locking member having an arcuate lower surface such that the bone screw is capable of flexion. Still another embodiment of the present invention provides for a locking member comprising a bone screw having a grooved collar engageable with a threaded inner surface of the countersink.

BRIEF DESCRIPTION OF THE DRAWINGS

FIG. 1 is a side elevation view of a portion of the human spinal column having a preferred embodiment of the medical appliance of the present invention inserted therein.

FIG. 2 is an exploded perspective view of a portion of the human spinal column having a preferred embodiment of the medical appliance of the present invention prior to attachment.

FIG. 2A is a side elevation view of a portion of the bottom plate of the present invention illustrating a screw barrel having an angled first end and a riveted second end.

DETAILED DESCRIPTION OF THE PREFERRED EMBODIMENT

Figure 3:
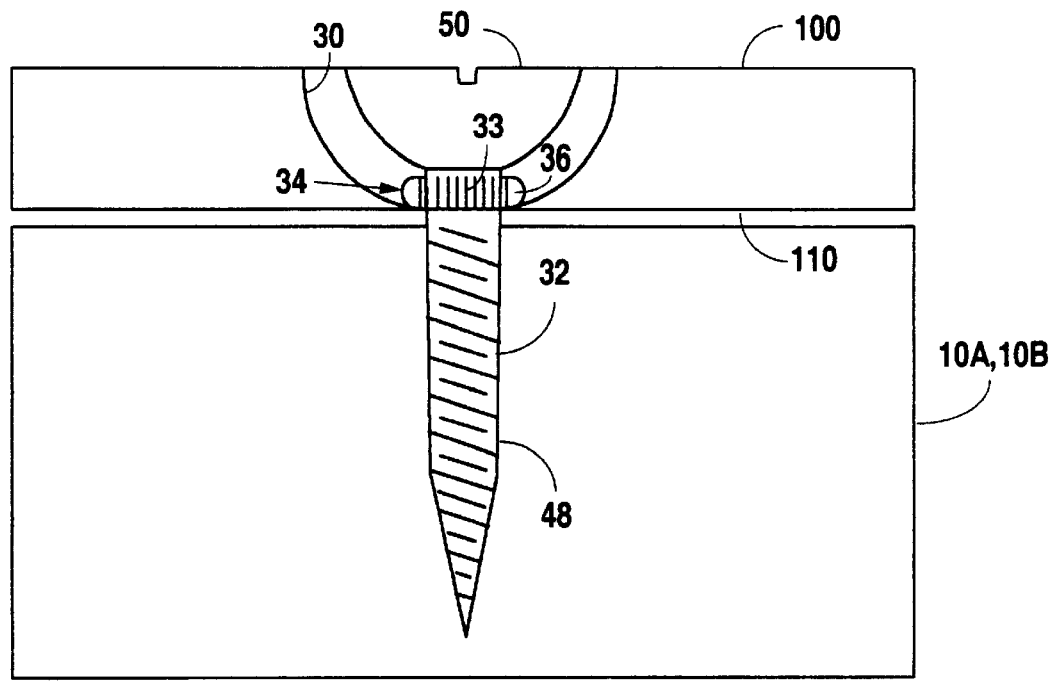
FIG. 3 is a side elevation view of an embodiment of the locking member of the present invention using a substantially circular locking ring attached to a substantially circular countersink.
Figure 3A:
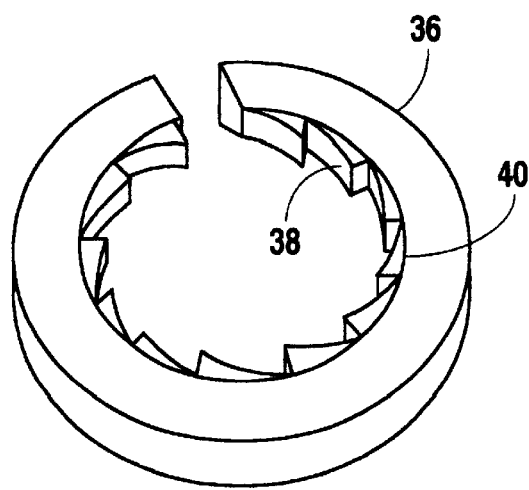
FIG. 3A is a perspective view of the locking ring of FIG. 3 illustrating the rachet teeth upon an interior surface of the locking ring.

The present invention is herein described as a medical appliance (100) adapted to bridge and stabilize spaced apart bone segments (10A and 10B, respectively), as a locking system for attaching a medical appliance to bone, and as a method for affixing a medical appliance (100) to bridge and stabilize spaced apart bone. Referring to the Figures, the spaced apart bone segments (10A and 10B, respectively) have outside surfaces (12A and 12B, respectively), ledge surfaces (14A and 14B, respectively), and inside surfaces (16A and 16B, respectively). Each ledge surface is a prepared surface used for the attachment of the bottom plate (18) to the bone segments (10A and 10B, respectively) as described below.

One embodiment of the present invention is shown implanted into the human spinal column in FIG. 1. The medical appliance of the present invention, indicated generally as reference numeral (100), is implanted into space between bone segments (10A and 10B, respectively) from which a portion of the vertebral body along with the intervertebral disk (11) has been removed, i.e. by diskectomy with corpectomy. The medical appliance has a bottom plate (18), a top plate (26), and a locking member (34).

Referring to FIGS. 1 and 2, the bottom plate (18) of the present invention is a rigid, elongate plate for spanning space (72) between bone segments (10A and 10B, respectively) and is attachable to the ledge surfaces (14A and 14B, respectively) of the bone segments. The bottom plate (18) has a bottom plate base (19) having a plurality of openings (24) for rotatably retaining a plurality of screw barrels (20). The screw barrels are substantially cylindrical in shape and extend from the bottom plate base (19) in a first direction. In one embodiment of the present invention, this first direction is away from the spinal cord (70) of the patient (not shown) such that the screw barrels may receive a barrel screw (22), as described below.

The medical appliance (100) of the present invention has a rigid, elongate top plate (26) having a top plate base (27). The top plate base has a plurality of slots (28) for receiving a plurality of barrel screws (22). The slots (28) are positioned and aligned upon the top plate base (27) such that barrel screws may be placed through the slots of the top plate (26) so they may extend in a second direction. In one embodiment of the present invention, this second direction is in the direction of the spinal cord (70), as shown in FIG. 1. This allows each barrel screw to engage a threaded inner surface (201) of each screw barrel (20) such that the top plate (26) and the bottom plate (18) may be fastened together. This allows the top and bottom plate to act in concert to bridge and stabilize the spaced apart bone segments (10A and 10B, respectively).

Referring to FIGS. 1, 2 and 2A, the screw barrel (20) may have an angled first end (20A) and a riveted second end (20B) in one embodiment of the present invention. The angled first end prevents disengagement of the screw barrel (20) from the opening (24) in the bottom base plate (19) by restricting movement of the screw barrel in a second direction toward the spinal cord (70).

Alternatively, the riveted second end (20B) of the screw barrel (20) prevents the disengagement of the screw barrel from the opening (24) by restricting movement in a first direction away from the spinal cord (70). The angled first end (20A) of the screw barrels also allows barrel screws (22) that are placed through the slots (28) of the top plate (26) to engage the screw barrels (20) of the bottom plate (18) at various angles. This allows the attachment of the medical appliance (100) to the bone segments (10A and 10B, respectively) to be stable and flexible.

The top plate (26) has a plurality of countersinks (30) for receiving bone screws (32) such that the top plate may be attached to the outside surfaces (12A and 12B, respectively) of each bone segment (10A and 10B, respectively). In one embodiment, the countersinks (30) are configured to receive bone screws (32) such that a bone screw inserted into a countersink may engage the outside surface (16) of the bone segment (10A and 10B, respectively), thus attaching the top plate (26) to the bone segment. The first and second ends (26A and 26B, respectively) are tapered such no sharp edges may contact the body of the patient (not shown).

The top (26) and bottom plates (18) of the present invention may be composed of any strong, thin, non-porous material such as carbon fiber, modified carbon, titanium, surgically compatible steel, physiologically inert and/or medically compatible polymers such as urethane or DELRIN® polymers, or any other substantially rigid surgical implant or biologically compatible material. On one embodiment, the top plate (26) is longer than the bottom plate (18) such that the top plate attaches to the outside surfaces (12A and 12B, respectively) of the bone segments and the bottom plate attaches to the ledge surface (14) of the bone segments (10A and 10B, respectively). The present invention allows both the top plate (26) and the bottom plate (18) to attach to each other and to the bone segments (10A and 10B), respectively, thus providing additional stability to the medical appliance (100).

If intervertebral fusion is desired, cancellous bone chips (not shown) may be formed into very fine particles such that they may be inserted and packed tightly into the space (72) between the bone segments (10A and 10B, respectively). The cancellous bone chips may then work in concert with the top (26) and bottom plate (18) of the medical appliance (100) to provide stability to the bone segments (10A and 10B, respectively). The present invention may also be used in concert with an artificial disk (not shown). This artificial disk may be used to fill the space between the bone segments (10A and 10B, respectively) and may be composed of any number of compressible physiologically inert and/or medically compatible polymers. For example, the disk may be composed of urethane or DELRIN® polymer for the purpose of providing shock absorption between the top plate (26) and the bottom plate (18).

Referring to FIGS. 3, 3A, 4 and 4A, in one embodiment of the present invention, the medical appliance (100) of the present invention has a locking member (34) disposed in each countersink (30). Each locking member engages each bone screw (32) to the medical appliance (100) such that axial and rotational movement of each bone screw is restricted. In one embodiment of the present invention, the locking member (34) is a locking ring (36) having a plurality of tapered, rachet teeth (38). The rachet teeth are located on an interior surface (40) of the locking ring (36) such that when the locking ring is attached to a countersink (30) of the top plate (26), the teeth are engageable with a serrated neck (33) of the bone screw (32) when the bone screw (32) is inserted through the countersink (30). The interplay between the teeth (38) and the serrated neck (33) allows the bone screw (32) to be placed into the countersink and racheted into the bone segment (10A and 10B, respectively). The bone screw is held in place by the teeth (38) once racheted into the bone segment. The taper of the teeth (38) of the locking ring (36) may be adjusted to vary the amount of torque required to remove the bone screw from the locking member (34).

Figure 4:
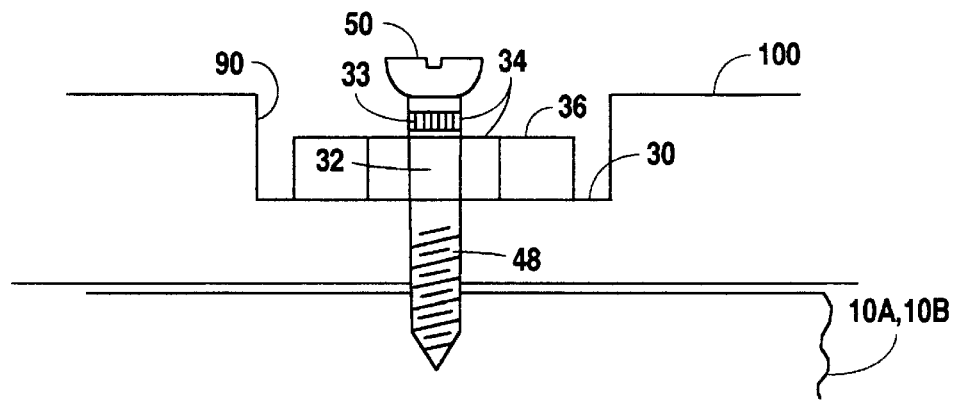
FIG. 4 is a side elevation view of an embodiment of the locking member of the present invention using a non-circular locking ring and a non-circular countersink.
Figure 4A:
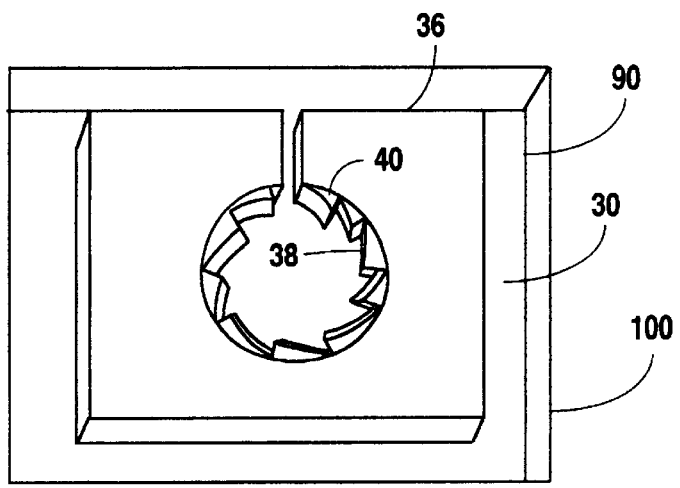
FIG. 4A is a perspective view of the locking ring of FIG. 4 illustrating the rachet teeth upon an interior surface of the locking ring.
Figure 4B:
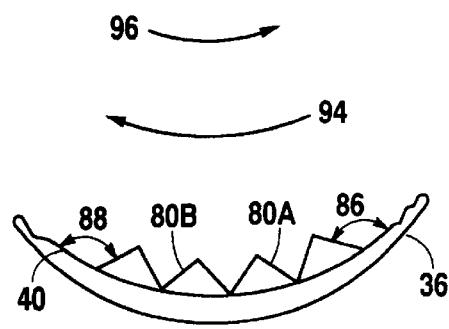
FIG. 4B is a top plan view of a portion of a locking ring illustrating the tapered rachet teeth.

Referring to FIG. 4B, each of the rachet teeth (38) has a leading edge (80A) and a trailing edge (80B). The taper of the leading edge (80A) controls the amount of torque required to rachet the bone screw (32) into the locking ring (36). For example, assuming the insertion of the screw into the locking ring (36) is accomplished by clockwise rotation (94), a leading edge taper angle (86) of about 90° with respect to the interior surface (40) of the locking ring (36) will not allow the bone screw (32) to rachet into the locking ring (36), as illustrated in FIG. 4B. A taper of about 90° will cause the serrations of the bone screw to perpendicularly contact the rachet teeth and block its clockwise rotation (94). However, an increase in the angle (86) of the leading edge (80A) with respect to the interior surface (40) to greater than 90° will allow the serrated neck (33) of the bone screw to rachet (32) within the locking ring (36), thus allowing sufficient clockwise rotation (94) of the bone screw to allow its insertion into the locking ring. The greater the taper of the leading edge (80A) above 90°, the less torque is required to insert the bone screw (32) into the locking ring (36) due to decreased resistance between the rachet teeth (38) and the serrations (33) of the bone screw (32).

Alternatively, the taper of the trailing edge (80B) controls the amount of torque required to rachet the bone screw (32) out of the locking ring (36). Assuming the removal of the bone screw from the locking ring (36) is accomplished by counter-clockwise rotation (96), a trailing edge taper angle (88) of about 90° with respect to the interior surface (40) of the locking ring (36) will not allow the bone screw to rachet out of the locking ring (36) in a counter-clockwise direction (96), as illustrated in FIG. 4B. A taper of about 90° will cause the serrations (33) on the bone screw (32) to perpendicularly contact the rachet teeth (38) and block its counter-clockwise rotation (96). However, an increase in the angle (88) of the trailing edge (80B) with respect to the interior surface (40) to greater than 90° will allow the serrated neck (33) of the bone screw (32) to rachet within the locking ring, thus allowing sufficient counter-clockwise rotation (96) of the bone screw (32) to allow its withdrawal from the locking ring (36). The greater the taper of the trailing edge (80B) above 90°, the less torque is required to remove the bone screw (32) from the locking ring (36) due to decreased resistance between the rachet teeth (38) and the serrations (33) of the bone screw (32). The taper angles of the leading and trailing edges (86 and 88, respectively) may be manipulated to provide varying degrees of stability for the bone screws (32).

Figure 5:
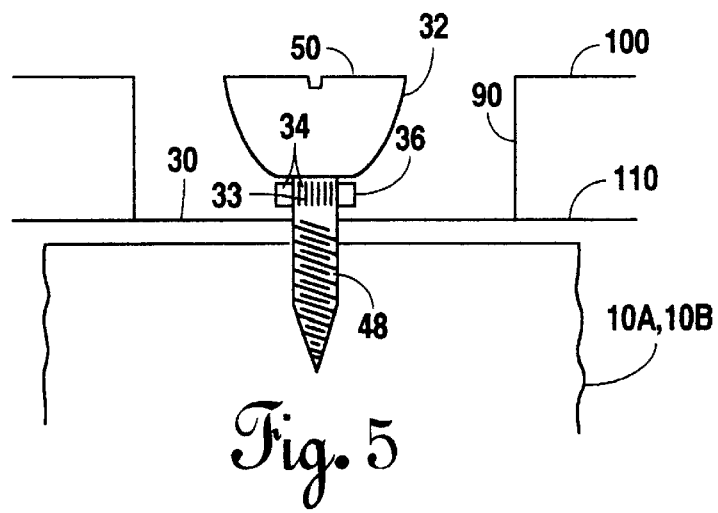
FIG. 5 is a side elevation view of an embodiment of the locking member of the present invention using a non-circular locking ring preassembled to the bone screw.

Both the locking ring (36) and the countersink (30) may have a substantially circular configuration or a non-circular configuration as illustrated in FIGS. 3–6. Referring to FIGS. 4, 4A and 5, one embodiment of the present invention uses a non-circular locking ring (36) having a plurality of tapered, rachet teeth (38) upon an interior surface (40) is used in conjunction with a non-circular countersink (30). The locking ring (36) may be attached directly to the bone screw (32) such that the teeth are engageable with a serrated neck (33) of the bone screw (32) upon insertion of the bone screw (32) through the countersink (30).

Figure 6:
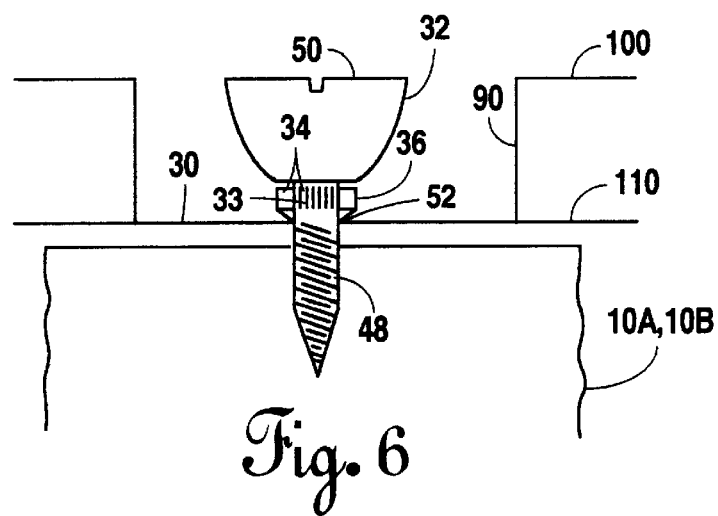
FIG. 6 is a side elevation view of an embodiment of the locking member of the present invention using a locking ring having an arcuate lower surface preassembled to the bone screw.

The locking ring rotates when the bone screw rotates due to the engagement of the teeth of the locking ring and the serrated neck of the bone screw (32). This non-circular configuration allows limited rotational movement of the bone screw without causing the bone screw to disengage from the bone segment (10A and 10B, respectively). The locking ring (36) is sized slightly smaller than the countersink (30) such that the locking ring may rotate along with the bone screw until it abuts side wall (90) of the countersink. Referring to FIG. 6, another embodiment of the present invention uses a locking ring having an arcuate lower surface (52) that allows limited flexion of the bone segment (10A and 10B, respectively) about the appliance once the bone screw (32) has been inserted through the countersink (30).

Figure 7:
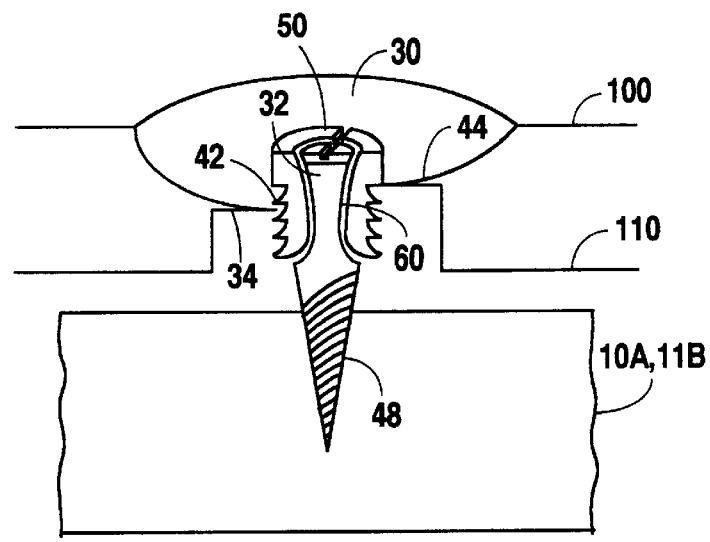
FIG. 7 is a side elevation view of an embodiment of the locking member of the present invention using a bone screw having a grooved collar for engaging a threaded inner surface of the countersink.

Referring to FIG. 7, another embodiment of the present invention uses a bone screw (32) having a grooved collar (42) for engaging a threaded inner surface (44) of the countersink (30) as a locking member (34). Engagement of the threaded inner surface and the collar allows for attachment of the bone screw to the countersink (30) of the medical appliance (100) but also provides for limited movement of the bone segment (10A, 10B) in relation to the appliance (100). An hour glass shaped orifice (60) located between the collar and the bone screw (32) allows limited bone segment (10A, 10B) movement while the engagement of the collar (42) and the threaded surface (44) allows rotational movement even though the collar remains engaged with the threaded surface of the countersink (30). The number of threads present upon the threaded inner surface (44) may be varied to provide for additional stability or range of motion. To illustrate, an increase in the number of threads contained by the threaded inner surface (44) will increase the stability of the locking member by allowing only limited rotation. Alternatively, a decrease in the number of threads will increase the range of rotation available to the collar (42) within the threaded inner surface allowing rotation of the collar (42) within the threaded inner surface (44).

Referring to the Figures, the present invention may also be described as a locking system used to attach a medical appliance (100) to bone. The locking system of the present invention has a plurality of countersinks (30) located within the base of the appliance (110). Each countersink (30) has an opening (46) for receiving a bone screw (32). The bone screw having a first threaded end (48), an opposite second end (50), and a serrated neck (33). The locking system also has a locking member (34) for engaging the bone screw (32) to the medical appliance (100) at its serrated neck (33) such that axial and rotational movement of the bone screw is restricted.

The bone screw (32) of the locking system may have a substantially spherical head end (50) or any other configuration that allows the screw to be secured to the countersink (30) of the medical appliance (100). Referring to FIGS. 3, 3A, 4, and 4A, in one embodiment of the present invention, the locking system of the present invention has a locking member (34) disposed in each countersink (30). Each locking member engages each bone screw (32) to the medical appliance (100) such that axial and rotational movement of each bone screw is restricted.

In one embodiment of the present invention, the locking member (34) of the locking system is a locking ring (36) having a plurality of tapered, rachet teeth (38) working in conjunction with a serrated neck (33) of a bone screw (32). The rachet teeth are located on an interior surface (40) of the locking ring (36) such that when the locking ring is attached to a countersink (30) of the top plate (26), the teeth are engageable with a serrated neck (33) of the bone screw (32) when the bone screw (32) is inserted through the countersink (30). The interplay between the teeth (38) and the serrated neck (33) allows the bone screw (32) to be placed into the countersink and racheted into the bone segment (10A and 10B, respectively). The bone screw is held in place by the rachet teeth (38) once racheted into the bone segment. The taper of the teeth (38) of the locking member (34) may be adjusted to vary the amount of torque required to remove the bone screw from the locking member (34).

Referring to FIG. 4B, each of the rachet teeth (38) has a leading edge (80A) and a trailing edge (80B). The taper of the leading edge (80A) controls the amount of torque required to rachet the bone screw (32) into the locking ring (36). For example, assuming the insertion of the screw into the locking ring (36) is accomplished by clockwise rotation (94), a leading edge taper angle (86) of about 90° with respect to the interior surface (40) of the locking ring (36) will not allow the bone screw (32) to rachet into the locking ring (36), as illustrated in FIG. 4B. A taper of about 90° will cause the serrations of the bone screw to perpendicularly contact the rachet teeth and block its clockwise rotation (94). However, an increase in the angle (86) of the leading edge (80A) with respect to the interior surface (40) to greater than 90° will allow the serrated neck (33) of the bone screw to rachet (32) within the locking ring (36), thus allowing sufficient clockwise rotation (94) of the bone screw to allow its insertion into the locking ring. The greater the taper of the leading edge (80A) above 90°, the less torque is required to insert the bone screw (32) into the locking ring (36) due to decreased resistance between the rachet teeth (38) and the serrations (33) of the bone screw (32).

Alternatively, the taper of the trailing edge (80B) controls the amount of torque required to rachet the bone screw (32) out of the locking ring (36). Assuming the removal of the bone screw from the locking ring (36) is accomplished by counter-clockwise rotation (96), a trailing edge taper angle (88) of about 90° with respect to the interior surface (40) of the locking ring (36) will not allow the bone screw to rachet out of the locking ring (36) in a counter-clockwise direction (96), as illustrated in FIG. 4B. A taper of about 90° will cause the serrations (33) on the bone screw (32) to perpendicularly contact the rachet teeth (38) and block its counter-clockwise rotation (96). However, an increase in the angle (88) of the trailing edge (80B) with respect to the interior surface (40) to greater than 90° will allow the serrated neck (33) of the bone screw (32) to rachet within the locking ring, thus allowing sufficient counter-clockwise rotation (96) of the bone screw (32) to allow its withdrawal from the locking ring (36). The greater the taper of the trailing edge (80B) above 90°, the less torque is required to remove the bone screw (32) from the locking ring (36) due to decreased resistance between the rachet teeth (38) and the serrations (33) of the bone screw (32). The taper angles of the leading and trailing edges (86 and 88, respectively) may be manipulated to provide varying degrees of stability for the bone screws (32).

Both the locking ring (36) and the countersink (30) of the locking system may have a substantially circular configuration or a non-circular configuration as illustrated in FIGS. 3–6. In one embodiment of the present invention, a non-circular locking ring (36) having a plurality of tapered, rachet teeth (38) upon an interior surface (40) is used in conjunction with a non-circular countersink (30). The locking ring (36) is attached to the bone screw (32) such that the teeth are engageable with a serrated neck (33) of the bone screw (32) upon insertion of the bone screw (32) through the countersink (30). The locking ring rotates when the bone screw rotates due to the engagement of the rachet teeth of the locking ring and the serrated neck of the bone screw (32). This non circular configuration allows limited rotational movement of the bone screw without causing the bone screw to disengage from the bone segment (10A and 10B, respectively). The locking ring (36) is sized slightly smaller than the countersink (30) such that the locking ring may rotate along with the bone screw until it abuts the countersink, thus allowing limited rotation. Referring to FIG. 6, another embodiment of the locking system of the present invention has a locking ring having an arcuate lower surface (52) that allows limited flexion of the bone screw (32) once it has been inserted through the countersink (30).

Referring to FIG. 7, another embodiment of the locking system of the present invention uses a bone screw (32) having a grooved collar (42) for engaging a threaded inner surface (44) of the countersink (30). Engagement of the threaded inner surface and the collar allows for attachment of the bone screw to the countersink (30) of the medical appliance (100) but also provides for limited movement of the collar (42) with respect to the countersink (30). An orifice (60) located between the collar and the bone screw (32) allows limited axial and flexion movement while the engagement of the collar (42) and the threaded surface (44) allows rotational movement of the screw collar even though the collar remains engaged with the threaded surface of the countersink (30). The number of threads present upon the threaded inner surface (44) may be varied to provide for additional stability or range of motion. To illustrate, an increase in the number of threads contained by the threaded inner surface (44) will increase the stability of the locking member by allowing only limited rotation. Alternatively, a decrease in the number of threads will increase the range of rotation available to the collar (42) within the threaded inner surface allowing rotation of the collar (42) within the threaded inner surface (44).

It is understood that each embodiment of the locking system described above may be used in combination with the apparatus described above or to affix any other medical appliance (100) to bone. The locking system described above may also be used to secure both the top plate (26) to the outside surfaces (12A and 12B, respectively) of the bone segments (10A and 10B, respectively) and the bottom plate (18) to the ledge surfaces (14A and 14B, respectively) of the bone segments.

The medical appliance (100) may be affixed to spaced apart bone segments (10A and 10B, respectively) by following a few simple steps. First, a first and second ledge surface (14A and 14B, respectively) is prepared on the spaced apart bones (10A and 10B, respectively). This may be accomplished by using any acceptable medical technique. A first and second end (18A and 18B, respectively) of the bottom plate (18) are then attached to the first and second ledge surfaces (14A and 14B, respectively) of the spaced apart bone segments (10A and 10B, respectively). A first end (26A) of the top plate (26) is attached to a first bone segment (10A) upon its outside surface (12A) and the second end (26B) of the top plate (26) is attached to a second bone segment (10B) at its outside surface (12B) using bone screws (32).

The screw barrels (20) of the bottom plate (18) are then aligned with the slots (28) of the top plate (26). The top plate may then be attached to the bottom plate (18) such that the barrel screws (22) extend through the slots (28) and engage the threaded inner surface (20I) of the screw barrels (20). The bone screws (32) are then locked to the medical appliance such that the teeth (38) of the locking ring (36) engage the serrated neck (33) of the bone screws (32).

The bone screws may be locked to the bone segments (10A and 10B, respectively) using several different locking members (34). A locking member (34) having a locking ring (36) attached to the bone screw (32) may be used to lock the bone screws to the appliance (100) such that rachet teeth (38) of the locking ring (36) engage a serrated neck (33) of each bone screw (32). A locking ring (36) with an arcuate lower surface that is pre-attached to the bone screw (32) may be used to lock the bone screws to the appliance (100) such that the rachet teeth (38) of the locking ring (36) engage a serrated neck (33) of the bone screws (32). A locking member (34) having a grooved collar (42) may be used to lock the bone screws (32) to the countersink (30) such that the collar engages a threaded inner surface (34) of the countersink.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A medical appliance adapted to bridge and stabilize spaced apart bone segments, said bone segments having an outside surface, a ledge surface, and an inside surface, said appliance comprising;
   a rigid, elongate bottom plate for spanning space between said bone segments, said bottom plate attachable to said ledge surface of said bone, said bottom plate further comprising;
   a bottom plate base;
   a plurality of screw barrels for receiving a plurality of barrel screws, said screw barrels extending from said bottom plate base in a first direction;
   a plurality of openings in said bottom base plate for rotatably retaining said screw barrels;
   a rigid, elongate top plate further comprising;
   a top plate base;
   a plurality of slots in said top plate base for receiving said plurality of barrel screws, said slots aligned to allow said barrel screws to engage said screw barrels of said bottom plate;
   a plurality of countersinks for receiving bone screws; and a locking member disposed in said countersink for engaging said bone screws to said medical appliance such that axial and rotational movement of said bone screws is restricted.

2. The appliance of claim 1, wherein said top plate is longer than said bottom plate.

3. The appliance of claim 1, wherein said screw barrel further comprises an angled first end and a second riveted end.

4. The appliance of claim 1, wherein said locking member further comprises a locking ring having a plurality of tapered rachet teeth on an interior surface, said locking ring attached to said top plate countersink, said teeth engagable with a serrated neck of said bone screw upon insertion through said countersink.

5. The appliance of claim 4, wherein said taper of said teeth may be adjusted to vary the amount of torque required to remove said bone screw from said locking member.

6. The appliance of claim 4, wherein said locking ring has a substantially circular configuration.

7. The appliance of claim 4, wherein said countersink has a substantially circular configuration.

8. The appliance of claim 1, wherein said locking member further comprises a non-circular locking ring having a plurality of tapered rachet teeth upon an interior surface, said locking ring attached to said bone screw such that said teeth may engage a serrated neck of said bone screw upon insertion of said bone screw through a non-circular countersink.

9. The appliance of claim 8, wherein said locking ring comprises an arcuate lower surface.

10. The appliance of claim 1, wherein said locking member comprises a bone screw having a grooved collar for engaging a threaded inner surface of said countersink.

11. A locking system for attaching a medical appliance to bone comprising:
    a countersink in said appliance, said countersink having an opening for receiving a bone screw having a threaded first end, an opposite second head end, and a serrated neck; and
    a locking member for engaging said bone screw to said medical appliance at said serrated neck such that axial and rotational movement of said bone screw is restricted.

12. The locking system of claim 11, wherein said head end is substantially spherical.

13. The appliance of claim 11, wherein said locking member further comprises a locking ring having a plurality of tapered rachet teeth on an interior surface, said locking ring attached to said top plate countersink said teeth engagable with a serrated neck of said bone screw upon insertion through said countersink.

14. The appliance of claim 13, wherein said taper of said teeth may be adjusted to vary the amount of torque required to remove said bone screw from said locking member.

15. The appliance of claim 13, wherein said locking ring comprises a substantially circular configuration.

16. The appliance of claim 13, wherein said countersink comprises a substantially circular configuration.

17. The appliance of claim 11, wherein said locking member further comprises a non-circular locking ring having a plurality of tapered rachet teeth upon an interior surface, said locking ring attached to said bone screw such that said teeth engages a serrated neck of said bone screw upon insertion of said bone screw through a non-circular countersink.

18. The appliance of claim 17, wherein said locking ring comprises an arcuate lower surface.

19. The appliance of claim 11, wherein said locking member comprises a bone screw having a grooved collar for engaging a threaded inner surface of said countersink.

20. A method for affixing a medical appliance to bridge and stabilize spaced apart bone comprising the steps of:
    preparing a first and second ledge surface on said spaced apart bones;
    providing a bottom plate comprising;
    a bottom plate base;
    a plurality of screw barrels for receiving a plurality of barrel screws, said screw barrels extending from said bottom plate base in a first direction;
    a plurality of openings in said base plate for rotatably retaining said screw barrels;

attaching a first end and a second end of said bottom plate to said first and said second ledge surfaces;

providing a top plate comprising;

a top plate base;

a plurality of slots in said top plate base for receiving said plurality of barrel screws, said slots aligned to allow said barrel screws to engage said screw barrels of said bottom plate;

a plurality of countersinks for receiving bone screws;

attaching a first and second end of said top plate to a first and second bone;

aligning said screw barrels of said bottom plate with said slots of said top plate; and attaching said top plate and said bottom plate such that said screws engage said screw barrels.

21. The method of claim 20, further comprising the steps of:

providing a locking member disposed in said countersink for engaging said bone screws to said medical appliance such that axial and rotational movement of said bone screws is restricted; and locking said bone screws to said appliance such that teeth of said locking member engage a serrated neck of said bone screws.

22. The method of claim 20, further comprising the steps of:

providing a locking member comprising a locking ring attached to said bone screw for engaging said bone screw to said medical appliance such that axial and rotational movement of said bone screw is restricted;

locking said bone screws to said appliance such that teeth of said locking ring engages a serrated neck of said bone screws.

23. The method of claim 20, further comprising the steps of:

providing a locking member comprising a locking ring having a lower arcuate surface, said locking ring attached to said bone screw for engaging said bone screw to said medical appliance such that axial and rotational movement of said bone screw is restricted;

locking said bone screws to said appliance such that teeth of said locking ring engages a serrated neck of said bone screws.

24. The method of claim 20, further comprising the steps of:

providing a locking member comprising a bone screw having a grooved collar for engaging a threaded inner surface of said countersink;

locking said bone screws to said appliance such that said collar engages a threaded inner surface of said countersink.

* * * * *